(12) United States Patent
Kunita et al.

(10) Patent No.: US 7,315,098 B2
(45) Date of Patent: Jan. 1, 2008

(54) LINEAR OSCILLATOR AND ELECTRICALLY DRIVEN TOOTHBRUSH

(75) Inventors: Tomohiro Kunita, Hikone (JP); Yoshihiro Kitamura, Hikone (JP); Hidekazu Yabuuchi, Hikone (JP); Hiroki Inoue, Hikone (JP); Masayuki Suzuki, Hikone (JP); Tomohiro Izumi, Hikone (JP); Tomio Yamada, Shiga (JP); Katsuhiro Hirata, Sanda (JP); Yasushi Arikawa, Neyagawa (JP); Yoshitaka Ichii, Kyoto (JP)

(73) Assignee: Matsushita Electric Works, Ltd., Osaka (JP)

( * ) Notice: Subject to any disclaimer, the term of this patent is extended or adjusted under 35 U.S.C. 154(b) by 479 days.

(21) Appl. No.: 10/472,188

(22) PCT Filed: Mar. 27, 2002

(86) PCT No.: PCT/JP02/02943

§ 371 (c)(1),
(2), (4) Date: Jan. 15, 2004

(87) PCT Pub. No.: WO02/078157

PCT Pub. Date: Oct. 3, 2002

(65) Prior Publication Data

US 2004/0128781 A1    Jul. 8, 2004

(30) Foreign Application Priority Data

Mar. 27, 2001 (JP) .............................. 2001-091318

(51) Int. Cl.
*A61C 17/16* (2006.01)
*A61C 17/34* (2006.01)
*H02K 33/04* (2006.01)
*H02K 33/00* (2006.01)

(52) U.S. Cl. ............................ 310/15; 310/20; 15/22.1; 15/22.2; 15/26

(58) Field of Classification Search ................ 15/22.1, 15/22.2, 26; 310/12, 15, 47, 20, 28, 36–38
See application file for complete search history.

(56) References Cited

U.S. PATENT DOCUMENTS 3,113,226 A * 12/1963 Moret .......................... 310/38

(Continued)

FOREIGN PATENT DOCUMENTS

EP            0580117            1/1994

(Continued)

OTHER PUBLICATIONS

Computer generated English translation of JP 9-252843, Sep. 1997.*

(Continued)

*Primary Examiner*—Laura Guidotti
(74) *Attorney, Agent, or Firm*—Greenblum & Bernstein, P.L.C.

(57) ABSTRACT

A linear oscillator and an electric toothbrush capable of emitting a low noise and of being assembled compact are provided. The linear oscillator, which reciprocates a shaft in an axial direction thereof, includes a plunger movable together with the shaft in the axial direction of the shaft, an elastic member for applying an axially acting resilient force to the plunger, an electromagnetic driving unit operable to reciprocate the plunger in the axial direction of the shaft at a resonant frequency when an alternating current is supplied thereto, and a fixing member restricting rotation of the plunger about an axis thereof within a predetermined angle. The electric toothbrush includes the linear oscillator and a brush head attached to the shaft for use in brushing teeth.

17 Claims, 13 Drawing Sheets

U.S. PATENT DOCUMENTS

| | | | |
|---|---|---|---|
| 3,149,255 A * | 9/1964 | Trench | 310/30 |
| 4,583,027 A * | 4/1986 | Parker et al. | 318/128 |
| 5,434,549 A | 7/1995 | Hirabayashi et al. | |
| 5,921,134 A | 7/1999 | Shiba et al. | |
| 6,098,288 A | 8/2000 | Miyagawa et al. | |
| 6,606,755 B1 * | 8/2003 | Robinson et al. | 15/105 |
| 6,873,067 B2 * | 3/2005 | Ichii et al. | 310/15 |
| 6,958,553 B2 * | 10/2005 | Ichii et al. | 310/15 |
| 2004/0010871 A1 * | 1/2004 | Nishinaka et al. | 15/22.2 |
| 2006/0158048 A1 * | 7/2006 | Kobayashi et al. | 310/12 |

FOREIGN PATENT DOCUMENTS

| | | | |
|---|---|---|---|
| JP | 6-7222 | | 1/1994 |
| JP | 7-177932 | | 7/1995 |
| JP | 9-252843 | * | 9/1997 |
| JP | 10115284 | | 5/1998 |
| JP | 10243622 | | 8/1998 |
| JP | 11-89210 | | 3/1999 |
| JP | 2001-346816 | * | 12/2001 |

OTHER PUBLICATIONS

English translation of Abstract of JP 9-252843, Sep. 1997 (also Derwent-Acc-No 1997-530208).*

English translation of JP 9-252-843, Dec. 1999.*

English Language Abstract of JP 6-7222.

English Language Abstract of JP 11-89210.

English Language Abstract of JP 7-177932.

English Language Abstract of JP 10-115284.

English Language Abstract of JP 10-243622.

* cited by examiner

LINEAR OSCILLATOR AND ELECTRICALLY DRIVEN TOOTHBRUSH

TECHNICAL FIELD OF THE INVENTION

The present invention relates to a linear oscillator capable of reciprocating in an axial direction thereof, and an electric toothbrush utilizing the linear oscillator.

DESCRIPTION OF THE RELATED ART

Some of the electric toothbrushes have a plurality of operating modes such as, for example, a bass brush mode, in which a brush head is reciprocatingly moved back and forth, and a rolling brush mode, in which the brush head is reciprocatingly rotated about a longitudinal axis of the brush head. For operating the electric toothbrush under any one of the bass brushing and rolling modes, the electric toothbrush includes a linear oscillator in combination with a motion translating mechanism, which converts a rotary motion into a linear reciprocating motion, and vice versa, to thereby drive the brush head selectively in one of those two directions.

When the motion translating mechanism is utilized in the electric toothbrush, problems of the energy efficiency decreasing and of noises generated occur due to a mechanical loss of the motion translating mechanism and, also, downsizing of the electric toothbrush is difficult to achieve. Furthermore, since in the electric toothbrush the direction of motion of the motor shaft is generally different from the direction of movement of the brush head, a bending moment occurs during the operation of the motor with the driving characteristic of the electric toothbrush adversely affected consequently.

The present invention has been developed to overcome the above-described disadvantages and has an objective to provide a linear oscillator and an electric toothbrush utilizing the linear oscillator capable of being operated at a high efficiency, emitting low noises during the operation and being downsized.

DISCLOSURE OF THE INVENTION

In accomplishing the above and other objectives, a linear oscillator according to the present invention reciprocates a shaft in an axial direction of the shaft, and includes a plunger movable together with the shaft in the axial direction of the shaft, an elastic member for applying to the plunger a resilient force acting in the axial direction of the shaft, an electromagnetic driving unit for reciprocatingly driving the plunger in the axial direction of the shaft at a resonant frequency when an alternating current is applied to such electromagnetic driving unit, and a fixing member for restricting a rotation of the plunger about an axis thereof within a predetermined angle. Accordingly, an electric energy can be directly transformed into a linear reciprocating motion of the moving part, which includes the plunger and the shaft, and, thus, the electric toothbrush of the present invention requires no motion translating mechanism capable of translating the rotary motion into the linear motion. Moreover, since the alternating current at a resonant frequency is supplied, features of high efficiency, low noise and downsizing can readily be accomplished. Such linear oscillator can advantageously be employed as a driving unit for, for example, a mechanical controller, an electric razor and an electric toothbrush. Further, the linear oscillator makes use of a restricting means for restricting the angle of rotation of the shaft about the axis thereof and, therefore, it is possible to cause the moving part to reciprocatingly move along a straight path.

The electromagnetic driving unit may include a magnet for supplying a magnetic force to the plunger in the axial direction of the shaft, a coil for varying the magnetic flux density of the magnet in dependence on an electric current flowing therethrough, and a control circuit for supplying an alternating current of a resonant frequency to the coil to vary the balance between the resilient force of the elastic member and the magnetic force of the magnet, thereby reciprocating the plunger in the axial direction of the shaft.

The elastic member may be a coil spring operable to rotate the shaft about an axis thereof within the predetermined angle, which is defined by the fixing member, in dependence on a change in axial length of the coil spring caused by the reciprocating motion of the plunger. Accordingly, not only the linear reciprocating motion of the shaft in the axial direction thereof, but also the rotary motion of the shaft about the axis thereof in synchronization with the linear reciprocating motion can be obtained. Therefore, the brush head can undergo a linear vibration for the "Bass" brush mode and a rolling motion for the rolling brush mode, one at a time.

The electric toothbrush according to the present invention has a linear oscillator for reciprocating the shaft in the axial direction thereof and the brush head attached to the shaft for use in brushing teeth, and the linear oscillator includes a plunger movable together with the shaft in the axial direction of the shaft, an elastic member for applying a resilient force to the plunger in the axial direction of the shaft, an electromagnetic driving unit supplied with an alternating current to reciprocate the plunger in the axial direction of the shaft at a resonant frequency, and a fixing member for restricting a revolution of the plunger about its own longitudinal axis within a predetermined angle. Accordingly, it is possible to obtain the previously described effects of the linear oscillator and, at the same time, since an occurrence of bending moment that will bring about adverse effects on the driving characteristic can be reduced, it is also possible to use an energy at high efficiency. Moreover, when the brush head reciprocates, the shaft directly drives the brush head so that the brushing operation can be carried out highly efficiently with the minimized number of components. Therefore, the brush head can only and surely reciprocates along the straight line.

The electromagnetic driving unit may include a magnet for supplying a magnetic force to the plunger in the axial direction of the shaft, a coil for varying a magnetic flux density of the magnet in dependence on a current flowing therethrough, and a control circuit for supplying an alternating current at a resonant frequency to vary the balance between the resilient force of the elastic member and the magnetic force of the magnet, thereby reciprocating the plunger in the axial direction of the shaft.

The elastic member may be a coil spring operable to rotate the shaft about the axis thereof within the predetermined angle, which is defined by the fixing member in dependence on expansion and contraction of the coil spring caused by the reciprocating motion of the plunger. Accordingly, the brush head can accomplish easily the "Bass" brush motion and the rolling brush motion.

The control circuit may regulate the pulse width of an electric power pulse, required to obtain the alternating current, to vary the stroke of reciprocating motion of the plunger in the axial direction of the shaft. Therefore, the motion of the brush head can be adjusted to the taste of a user of the electric toothbrush.

The control circuit may vary the timing at which an electric power pulse required to obtain the alternating current, in dependence on the length of time elapsed subsequent to the start of the reciprocating motion of the plunger. Accordingly, the user can know how long the user brushes the teeth.

The control circuit may gradually increase the pulse width of an electric power pulse, required to obtain the alternating current, in dependence on the length of time elapsed subsequent to the start of the reciprocating motion of the plunger, thereby increasing the stroke of reciprocating motion in the axial direction of the shaft. Therefore, even if the user turns the power supply on before the user starts brushing in his or her mouth, there is no possibility that a tooth powder and water applied to the brush head may scatter.

DETAILED DESCRIPTION OF THE PREFERRED EMBODIMENTS

Figure 1A:
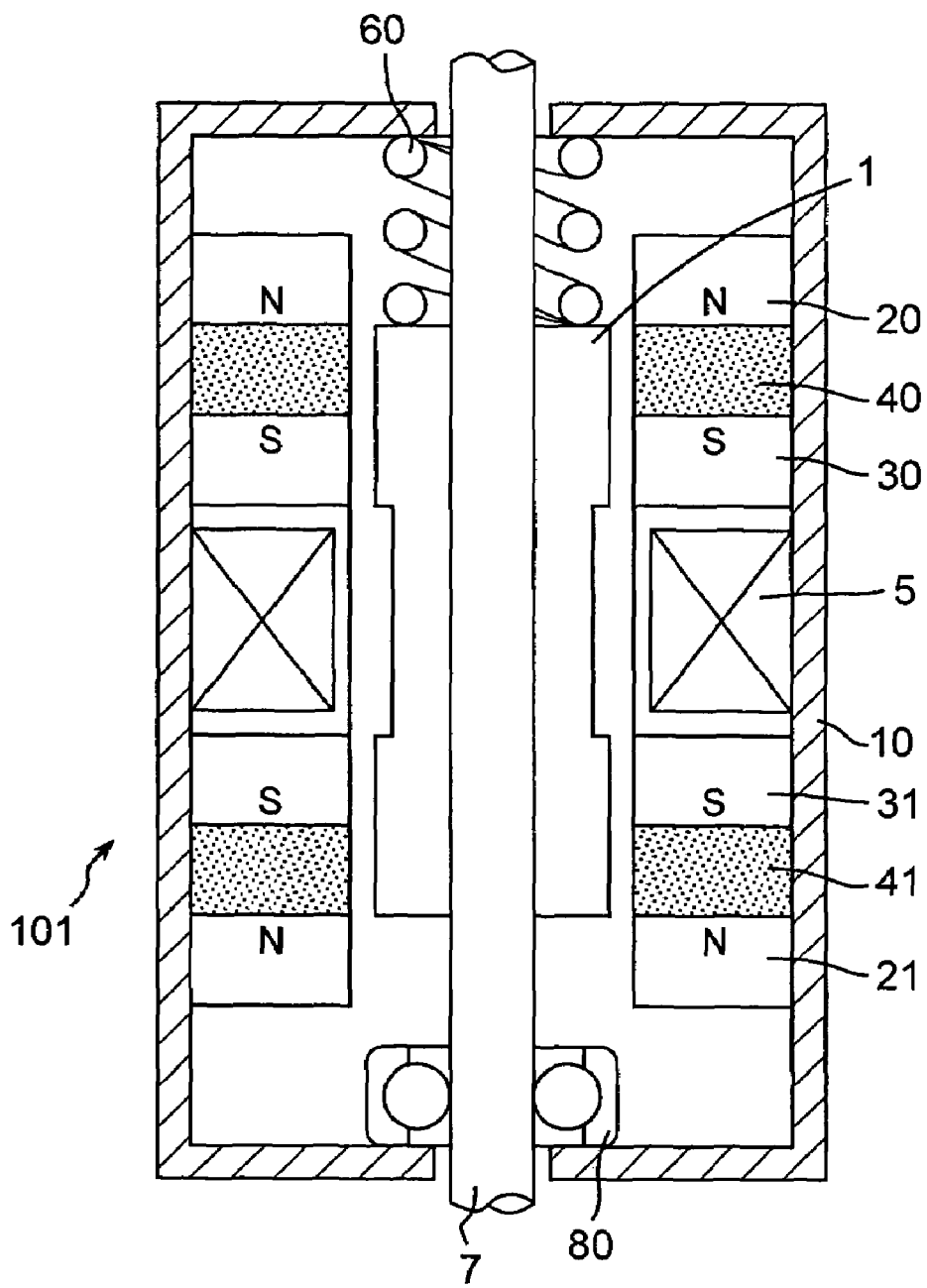
FIG. 1A is a longitudinal sectional view of the structure of a linear oscillator according to a first embodiment of the present invention.

Various embodiments of the present invention will be described below in detail with reference to the accompanying drawings. In those drawings, elements given the same reference numeral have the same function.

FIG. 1A is a longitudinal sectional view showing the structure of a linear oscillator according to a first embodiment of the present invention. The linear oscillator 101 includes a moving part 1 fixed to a shaft 7. When the linear oscillator 101 is supplied with a predetermined electric current, the moving part 1 reciprocates together with the shaft 7 in an axial direction of the shaft. That is to say, supplying a predetermined current to the linear oscillator 101 allows the linear oscillator 101 to reciprocate the shaft 7. The linear oscillator 101 is employed as a driving source for accomplishing a "Bass" brush mode, in which a brush head in the case of, for example, an electric toothbrush is repeatedly reciprocatingly driven within a narrow stroke to generate a mechanical vibration.

Figure 1B:
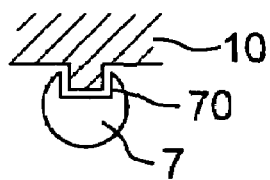
FIG. 1B is a partial cross-sectional view of the linear oscillator.

Description will be given hereinafter in detail of respective elements of the linear oscillator 101. The linear oscillator 101 includes a plunger 1 corresponding in function to the moving part, a coil 5, the shaft 7, a shield case 10, two first yokes 20 and 21, two second yokes 30 and 31, two permanent magnets 40 and 41, a coil spring 60 and a shaft bearing 80. The plunger 1 is made of a magnetic material such as, for example, iron so as to assume a cylindrical shape, and has a relatively large diameter in the vicinity of the respective ends of the plunger 1 and a smaller diameter at a portion thereof intermediate between the opposite ends of the plunger 1. The plunger 1 is secured to the shaft 7 for movement together with the shaft 7 in a direction axially of the shaft 7. The coil 5 is formed in an annular shape and is disposed within the shield case 10 so as to encircle an outer periphery of the plunger 1. As will be described below, supply of an electric current through the coil 5 causes the plunger 1 to reciprocate together with the shaft 7 in the axial direction of the shaft 7. The shaft 7 forms a shaft of an electric toothbrush (not illustrated) and extends through the linear oscillator 101. FIG. 1B is a partial cross-sectional view showing the cross-section of the linear oscillator taken in a direction perpendicular to the shaft. The shaft 7 is formed with a groove 70. Engagement between the groove 70 formed in the shaft 7 and a projecting member formed on the shield case 10 restricts a rotation of the shaft 7 relative to the plunger 1 about the shaft 7.

The first yokes 20 and 21 and the second yokes 30 and 31 are all formed in an annular shape. The permanent magnets 40 and 41 are also formed in an annular shape and are magnetized. The first yokes 20 and 21 are disposed on respective sides of the coil 5 symmetrically with respect to the coil 5. The second yokes 30 and 31 and the permanent magnets 40 and 41 are also disposed on respective sides of the coil 5 symmetrically with respect to the coil 5. When only one side of the coil 5 in an axial direction of the shaft 7 is considered, the disposition of the yoke 30, the permanent magnet 40 and the yoke 20 is arranged in this order from the position near the coil 5. This disposition is the same to the yoke 31, the permanent magnet 41 and the yoke 21 on the other side of the coil 5.

The spring 60 is a coil spring which forms a resilient element, and is interposed between the internal surface of the shield case 10 and one end of the plunger 1. That is to say, the spring 60 is fixed at one end to the shield case 10 and at the other end to the plunger 1. The spring 60 expands axially in response to axial movement of the plunger 1, to thereby apply an axially acting resilient force, i.e., a compressive force or a pulling force to the plunger 1. The magnitude and the direction of the resilient force are determined in dependence on the amount of axial movement of the plunger 1 and the spring constant. The shaft bearing 80 is arranged to the opposite end of the shield case 10 and holds the end of the shaft 7 axially slidably. Accordingly, the plunger 1 and the shaft 7 are capable of reciprocating in the axial direction of the shaft 7 relative to the shield case 10 of the linear oscillator 101.

The operation of the linear oscillator 101 will be described below. So long as no electric current is supplied to the coil 5, the plunger 1 stands motionless at the illustrated position where the axially acting magnetic force exerted by the permanent magnets 40 and 41 on the plunger 1 through the yokes 20, 30, 21 and 31 is balanced with the axially acting resilient force of the spring 60. When an electric current is supplied to the coil 5 so as to flow therethrough in one direction, the magnetic flux of either one of the two permanent magnets 40 and 41 is weakened and, thus, the plunger 1 moves toward the other of those permanent magnets together with the shaft 7 against the resilient force of the spring 60. On the other hand, when the supplied electric current flows through the coil 5 in the other direction counter to the above described direction, the plunger 1 moves in the opposite direction together with the shaft 7 against the resilient force of the spring 60. Accordingly, so long as the coil 5 is supplied with an alternating current that alternates its flowing direction one after the other, the plunger 1 and the shaft 7 can reciprocate in an axial direction of the shaft 7. Moreover, if the alternating current of a frequency in the vicinity of a resonant frequency, the reciprocating motion that takes place in a resonant state can be realized. The permanent magnets 40 and 41, the coil 5 and a control circuit for supplying the alternating current (for example, a driving control circuit 109 (illustrated in FIG. 9) as described below) are also called an electromagnetic driving unit for reciprocating the plunger 1 in a direction of the shaft 7. It is noted that the resonant frequency is a frequency which is determined in dependence on the spring constant of the spring 60 and the mass of the moving part that includes the plunger 1 and the shaft 7.

Figure 2:
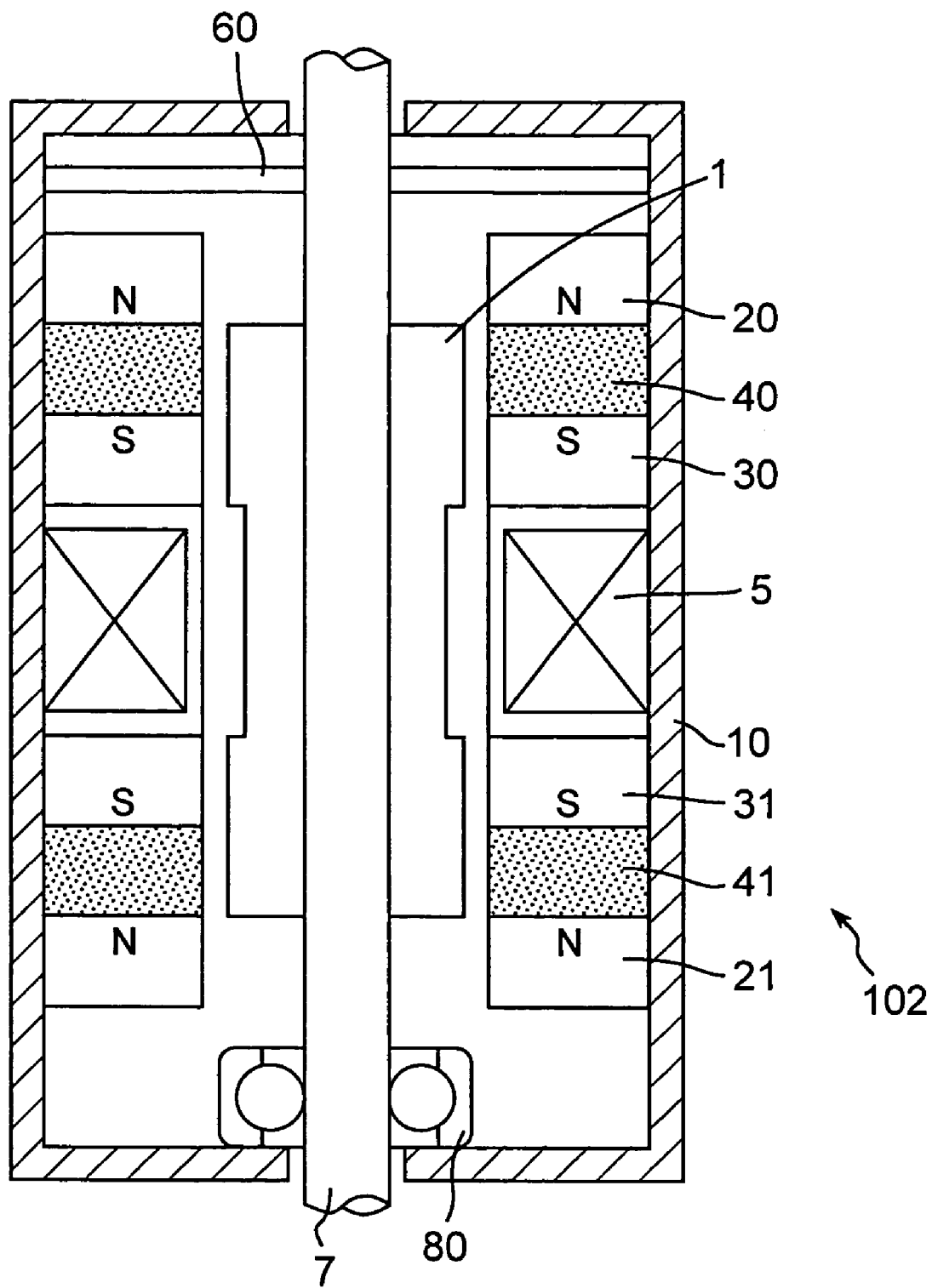
FIG. 2 is a sectional view of the structure of the linear oscillator utilizing a leaf spring according to a second embodiment of the present invention.

FIG. 2 is a sectional view showing a structure of the linear oscillator 102 including a leaf spring according to a second embodiment. The linear oscillator 101 (as illustrated in FIG. 1) has been described as having a coil spring as a preferred example of the spring 60. As illustrated in FIG. 2, however, the leaf spring 60 is in the form of a resilient plate (a leaf spring). This leaf spring 60 has an outer periphery fixed to the shield case 10 and an internal periphery fixed to the shaft 7. The leaf spring 60 does not only function as a spring, but also function as a rotation restricting member for restricting rotation of the shaft 7. Other structures of the linear oscillator 102 are identical with those of the linear oscillator 101 (as illustrated in FIG. 1). Therefore, the description of them is omitted.

Figure 3:
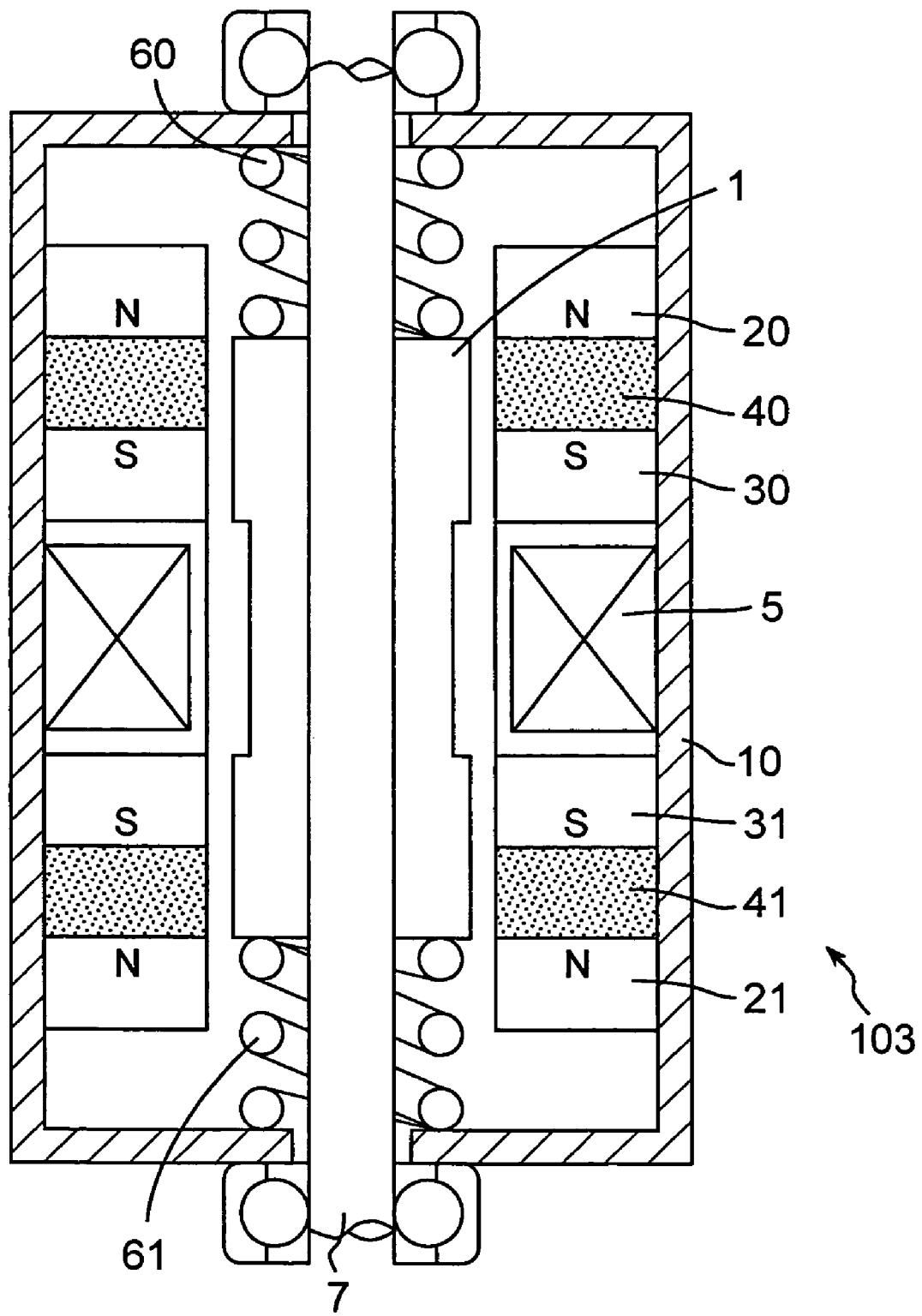
FIG. 3 is a sectional view of the structure of the linear oscillator utilizing two coil springs according to a third embodiment of the present invention.

FIG. 3 is a sectional view showing the structure of the linear oscillator 103 having two springs according to a third embodiment. This third linear oscillator 103 includes the coil spring 60 at one end of the shaft 7 and a coil spring 61 at the other end of the shaft 7. The coil spring 61 is interposed between the plunger 1 and the shield case 10. With this structure, the plunger 1 is biased by the two coil springs 60 and 61. Because of the employment of the springs 60 and 61, two shaft bearings are arranged on the outside of the shield case 10. It is to be noted that other structures of the linear oscillator 103 are identical with those of the linear oscillator 101 (as illustrated in FIG. 1).

Figure 4:
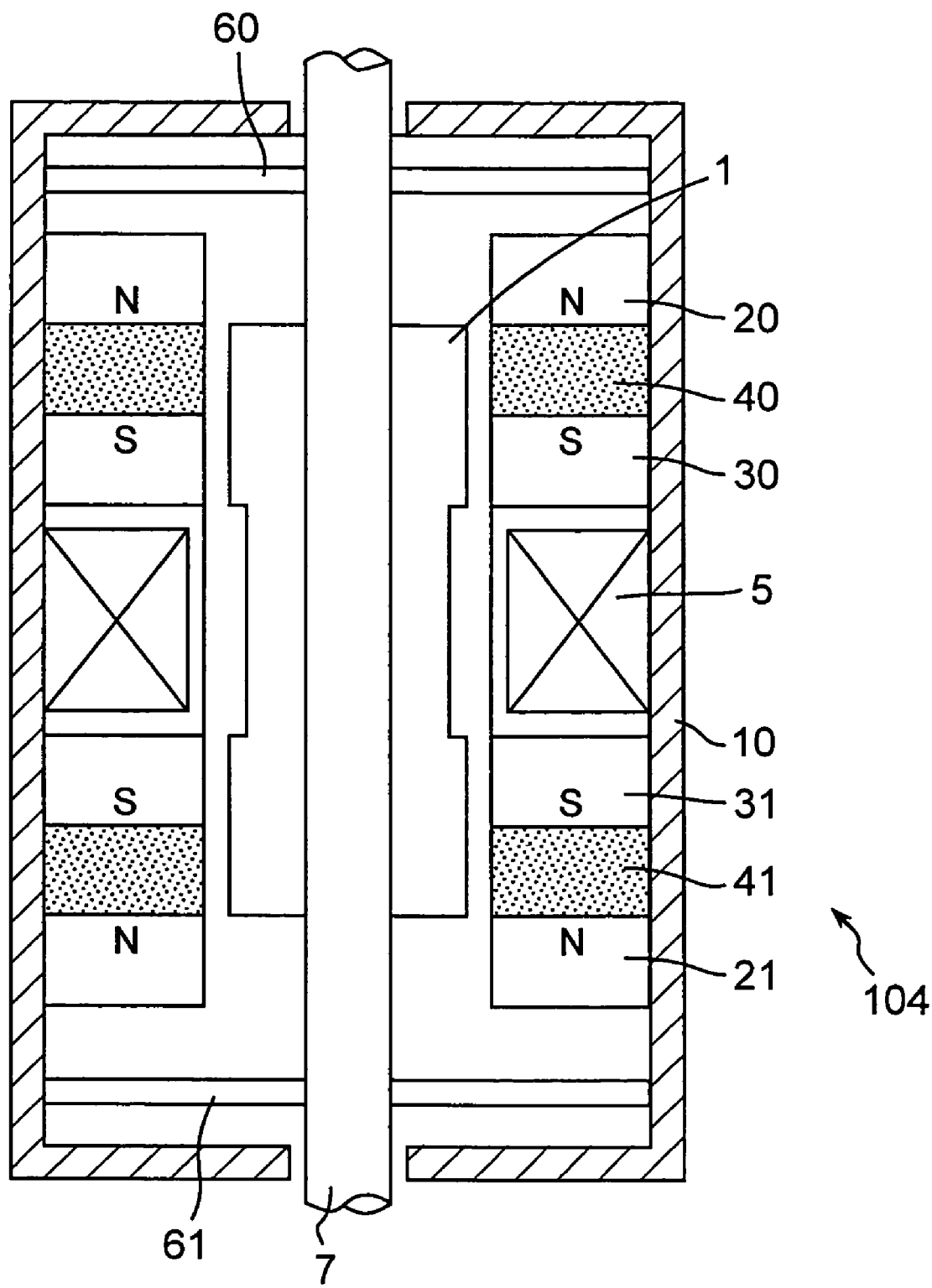
FIG. 4 is a sectional view of the structure of the linear oscillator utilizing two leaf springs according to a fourth embodiment of the present invention.

Leaf springs may be employed in the linear oscillator 103 instead of the coil springs 60 and 61. FIG. 4 is a sectional view showing the structure having two leaf springs employed in the linear oscillator 104 according to a fourth embodiment. That is to say, each of the springs 60 and 61 is employed in the form of a leaf spring in the linear oscillator 104.

Figure 5:
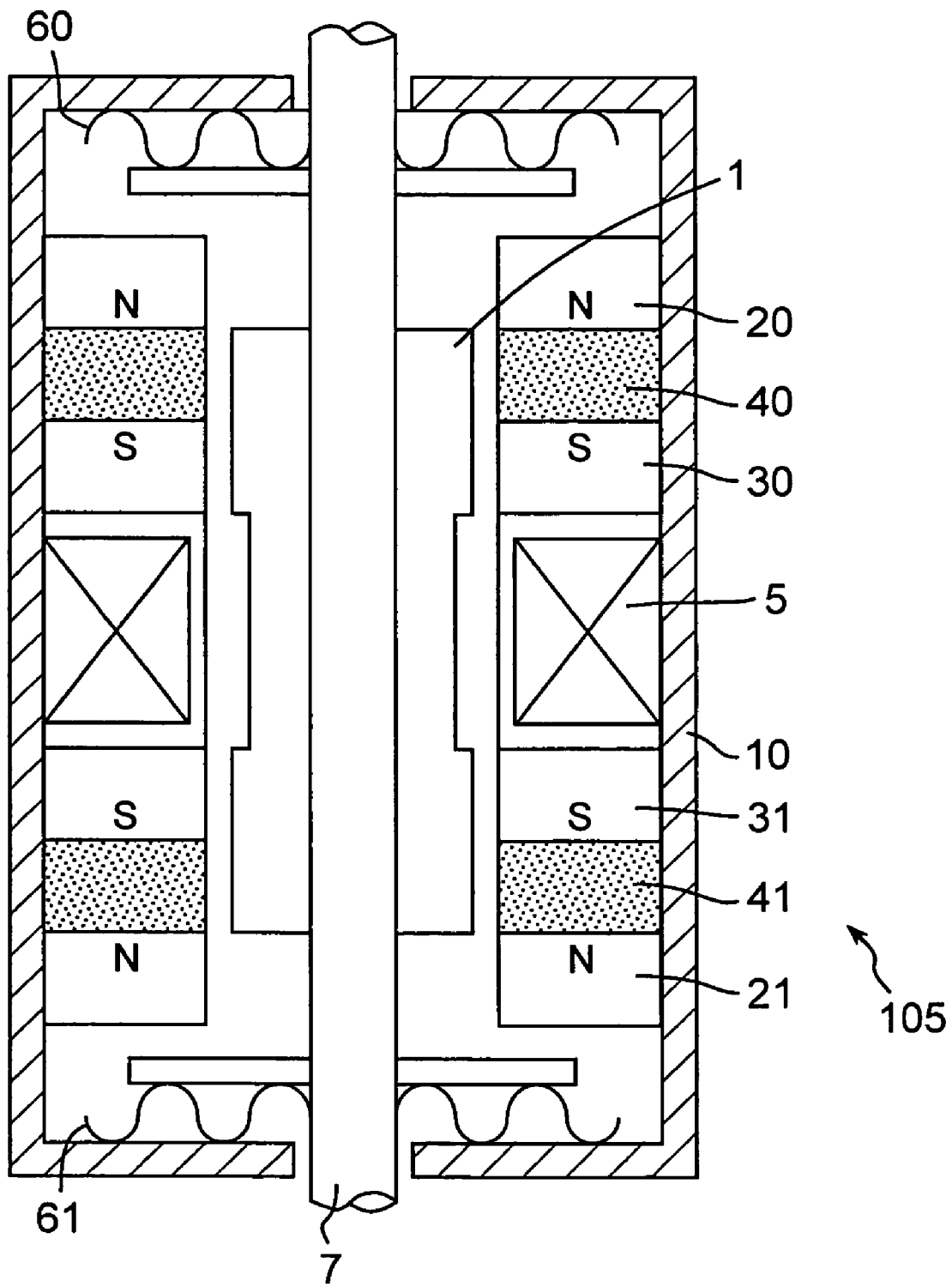
FIG. 5 is a sectional view of the structure of the linear oscillator utilizing two corrugated springs according to a fifth embodiment of the present invention.

Furthermore, other springs than the leaf spring may be employed. FIG. 5 is a sectional view showing the structure having two corrugated springs employed in the linear oscillator according to a fifth embodiment. The linear oscillator 105 reciprocates at a resonant frequency that is determined by the respective spring constants of the two springs 60 and 61 and the respective masses of the plunger 1 and the shaft 7. The linear oscillator 104 and 105 as illustrated respectively in FIG. 4 and FIG. 5 can support the shaft 7 without the shaft bearing 80 (such as illustrated in FIG. 1). In any of the embodiments described above, other structures of the linear oscillator are identical with those of the linear oscillator 101 (illustrated in FIG. 1).

Figure 6:
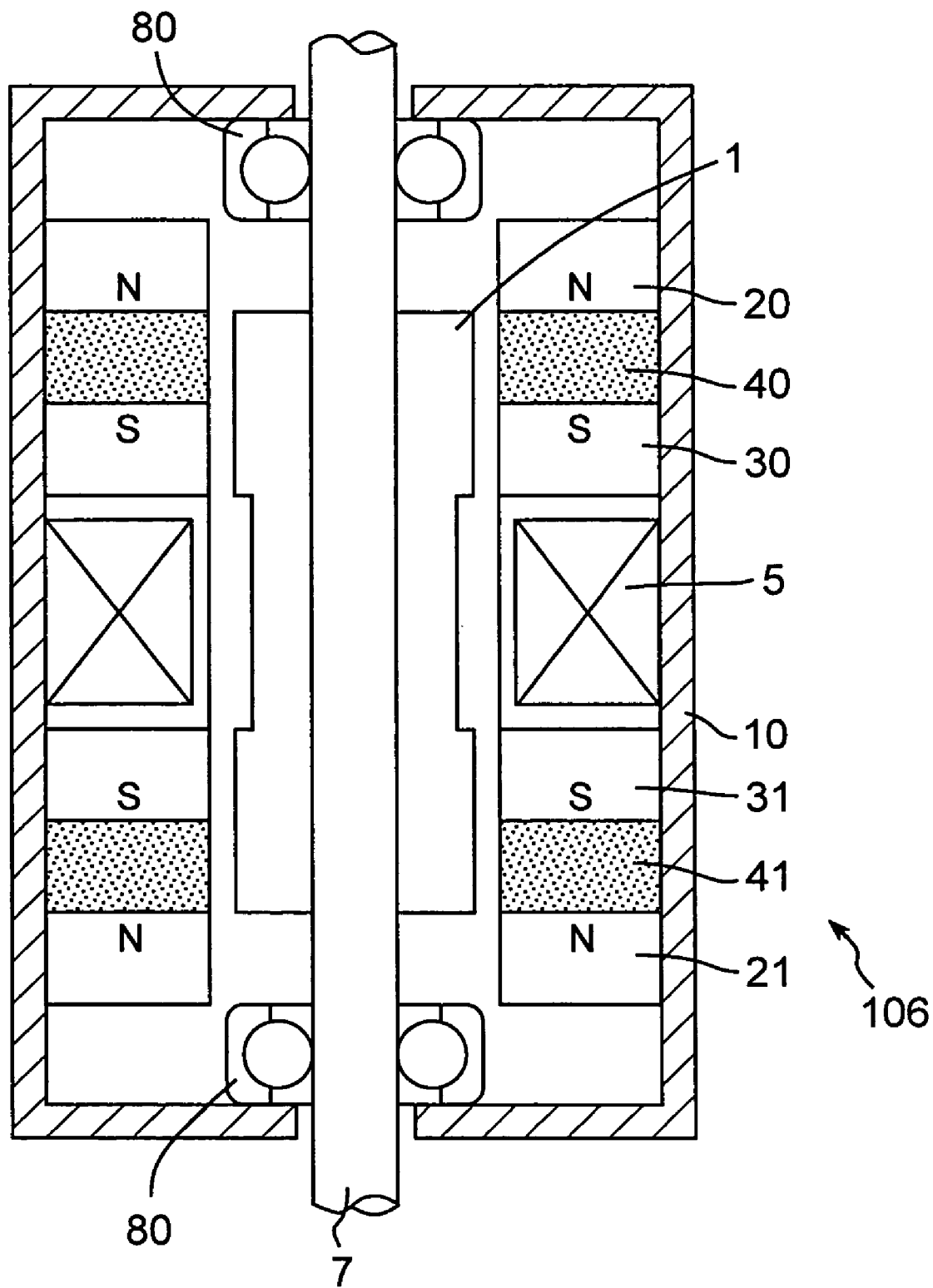
FIG. 6 is a sectional view of the structure of the linear oscillator according to a sixth embodiment of the present invention, in which no spring is employed.

It is noted that a detent force may be employed as a spring force for determining the resonant frequency. If the detent force is employed, the springs 60 and 61 will be dispensed with. FIG. 6 is a sectional view showing the structure of the linear oscillator 106 employing no spring according to a sixth embodiment.

Figure 7:
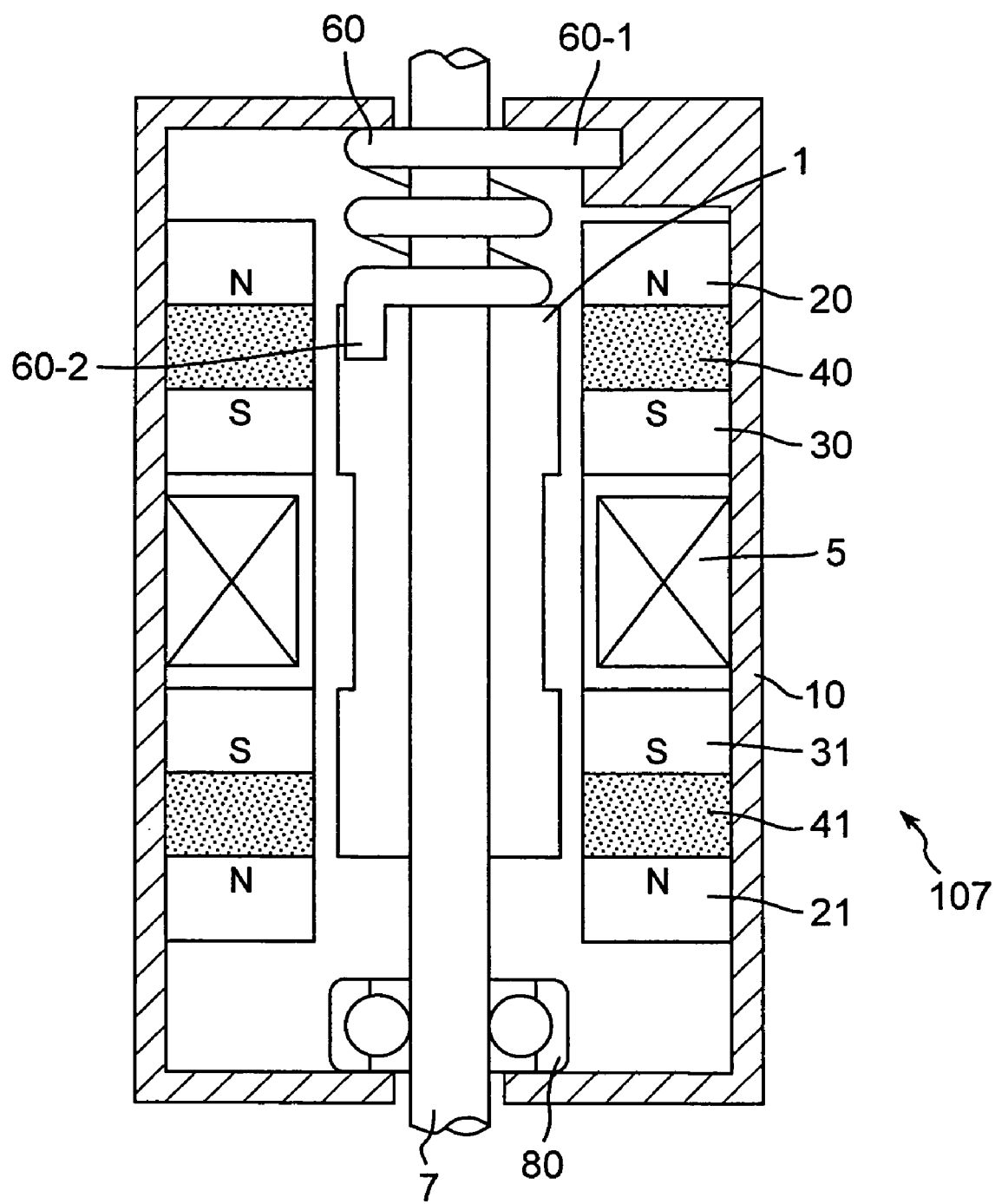
FIG. 7 is a sectional view of the structure of the linear oscillator according to a seventh embodiment of the present invention, in which a coil spring having two engaging members is employed.

FIG. 7 is a sectional view showing the structure of the linear oscillator 107 which is, in accordance with a seventh embodiment, provided with a coil spring 60 having two fixing portions 60-1 and 60-2. One end of the coil spring 60 is engaged with the shield case 10 to disable its rotation and serves as the fixing portion 60-1. The other end of the coil spring 60 is engaged with the plunger 1 to disable its rotation and serves as the fixing portion 60-2. With the use of the fixing portion 60-1 and 60-2, the coil spring 60 does not only exert the resilient force in an axial direction of the shaft 7 but also can allow the plunger 1 to rotate about the axis of the shaft 7 a small angle dependent on the amount of axial expansion or contraction, to thereby restrict further rotation of the plunger 1 beyond this small angle. It is to be noted that the small angle is preferably within the range from ±2 degrees to ±5 degrees and, more preferably up to an angle of ±2 degrees. Therefore, the linear oscillator 107 does not only reciprocate in the axial direction of the shaft 7 but also can reciprocatingly rotate within the small angle about the axis of the shaft 7. In addition, this rotation about the axis of the shaft 7 is similar to the case in which a torsion spring is added, and thus the resonance can be generated in the direction circumferentially of the shaft 7. It is to be noted that the linear oscillator capable of giving such an output, can be suitably employed as a driving source of the electric toothbrush, which requires the "Bass" brushing motion and the rotary (i.e. rolling) brushing motion.

By employing the above described linear oscillator as a linear oscillating motor, the electric toothbrush can be constituted. The electric toothbrush has a plurality of modes such as the "Bass" brushing, in which the brush head is reciprocatingly moved back and forth within the narrow stroke to generating a mechanical vibration, and the rotary brushing, in which the brush is reciprocatingly rotated. Such a structure and an operation of the electric toothbrush will now be described below.

Figure 8:
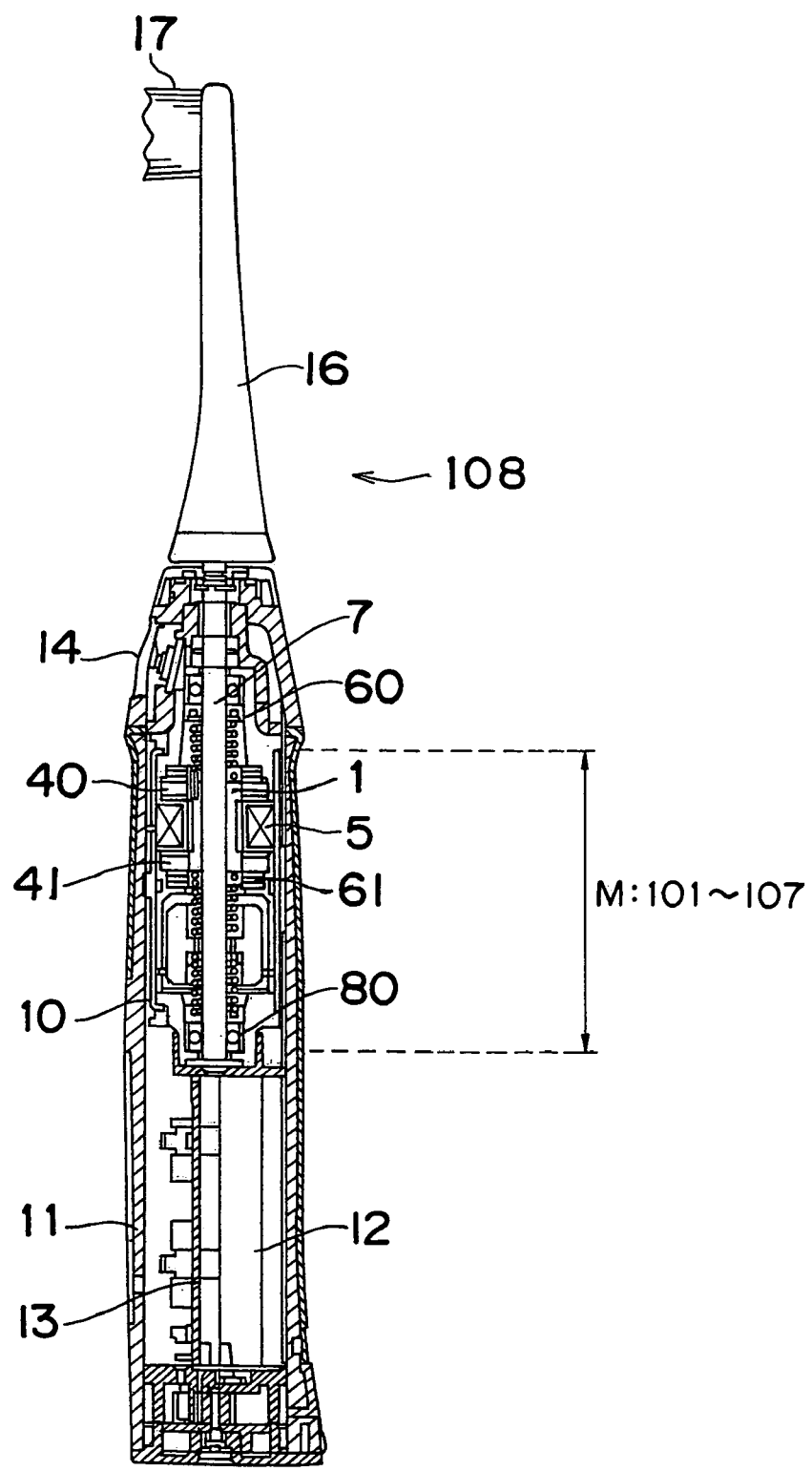
FIG. 8 is a sectional view of an embodiment of an electric toothbrush employing the linear oscillator according to the present invention.

FIG. 8 is a sectional view of the electric toothbrush 108 having a linear oscillator M as a driving source. The electric toothbrush 108 includes the linear oscillator M, a housing 11, a battery 12, a circuit board 13, a switch 14, a brush shank 16 and a brush head 17. These constituting elements of the electric toothbrush 108 are built within the housing 11 which is formed in a slender cylindrical shape or are disposed on an outer peripheral surface of the housing 11. Any one of the previously described linear oscillators 101 to 107 (illustrated respectively in FIGS. 1 to 7) may be employed for the linear oscillator M. The linear oscillator M is built within an upper section of the housing 11. The battery 12 is a primary battery or a secondary battery disposed as a power source in a lower section of the housing 11. The circuit board 13 is equipped with a driving control circuit of the linear oscillator M. The circuit board 13 and its driving control circuit are supplied with an electric power from the battery 12 and are electrically powered thereby. The switch 14 is disposed on an outer surface of the upper section of the housing 11 in the vicinity of the brush shank 16. The shaft 7 extending through the linear oscillator M projects outwardly from the upper end of the housing 11 and is coupled in line with the brush shank 16, which has the brush head 17 at a lateral surface thereof at a location remote from the housing 11.

Next, the operation of the electric toothbrush will be described. When linear oscillator M vibrates in the axial direction of the shaft 7 and, hence, the brush shank 16 that is coupled with the shaft 7 in line with each other, the brush shank 16 correspondingly vibrates in the axial direction of the shaft 7. Then the brush head 17 that is carried by the brush shank 16 undergoes vibration in the axial direction to accomplish the "Bass" brushing motion. When the linear oscillator 107 (illustrated in FIG. 7) is employed as the linear oscillator M, the plunger and the shaft additionally undergo a rolling motion besides the "Bass" brushing. Accordingly, the electric toothbrush 108 can realize a combined motion made up of a linear scrubbing motion and a rolling motion.

Figure 9:
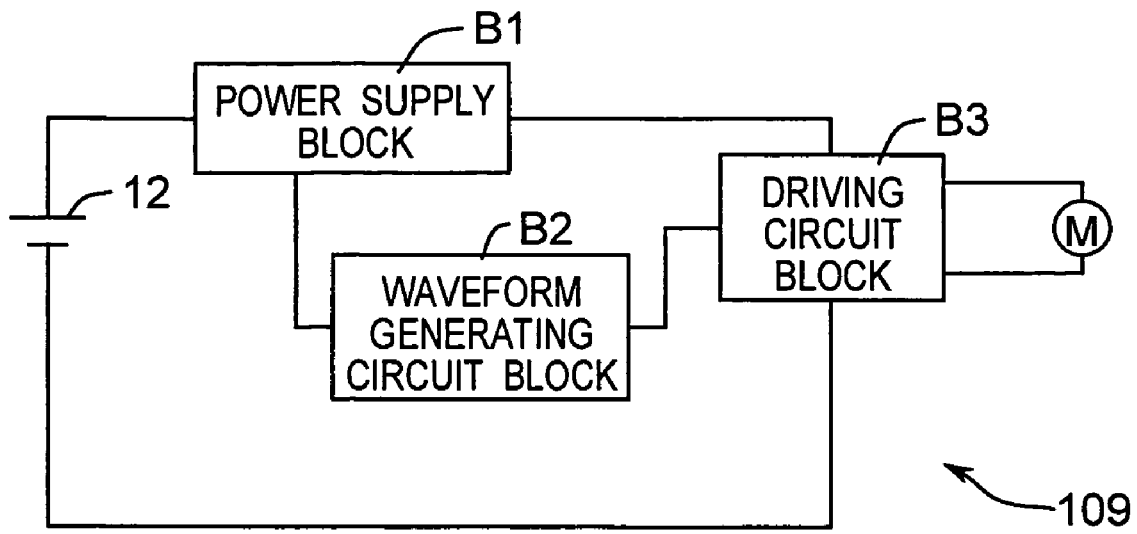
FIG. 9 is a block diagram showing the details of a driving control circuit.

The operation of the electric toothbrush 108 is regulated by the driving control circuit that is mounted on the circuit board 13. FIG. 9 is a block diagram showing the driving control circuit 109. The driving control circuit 109 includes a power supply block B1, a waveform generating circuit block B2 and a driving circuit block B3. As described above, the driving control circuit 109 is supplied with an electric power from the battery 12. The battery 12 and the power supply block B1 are electrically connected with each other by means of, for example, wiring on the circuit board 13. The power supply block B1 regulates an electric power from the battery 12 to provide an electric power to be supplied to the waveform generating circuit block B2. The waveform generating circuit block B2 generates a voltage waveform required to operate the linear oscillator M and then supplies it to the driving circuit block B3. The driving circuit block B3 includes a power element that supplies an electric power. The driving circuit block B3 controls the power element to provide an alternating current on the basis of a voltage signal of a predetermined waveform supplied from the waveform generating circuit block B2. Accordingly, it is possible to regulate the operation of the linear oscillator M such as vibration of the linear oscillator M.

The waveform generating circuit block B2 accommodates an electric drive energy control circuit (not illustrated), which regulates an electric drive energy. The electric drive energy control circuit controls either the amount of an electric current while the applied voltage is fixed or the applied voltage while the electric current is fixed, to thereby regulate the electric power. Description of how the electric drive energy control circuit regulates the electric energy will be given below with reference to the latter.

Figure 10:
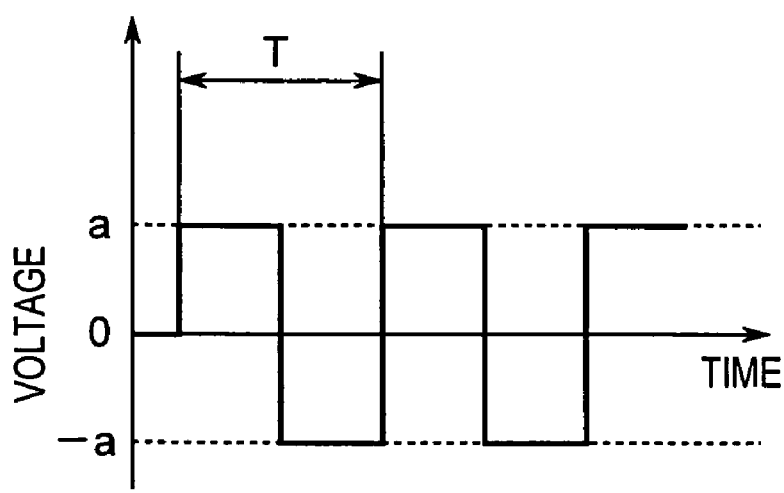
FIG. 10 is a chart showing the waveform of an output voltage supplied from an electric source block to a waveform generating circuit block.
Figure 11A:
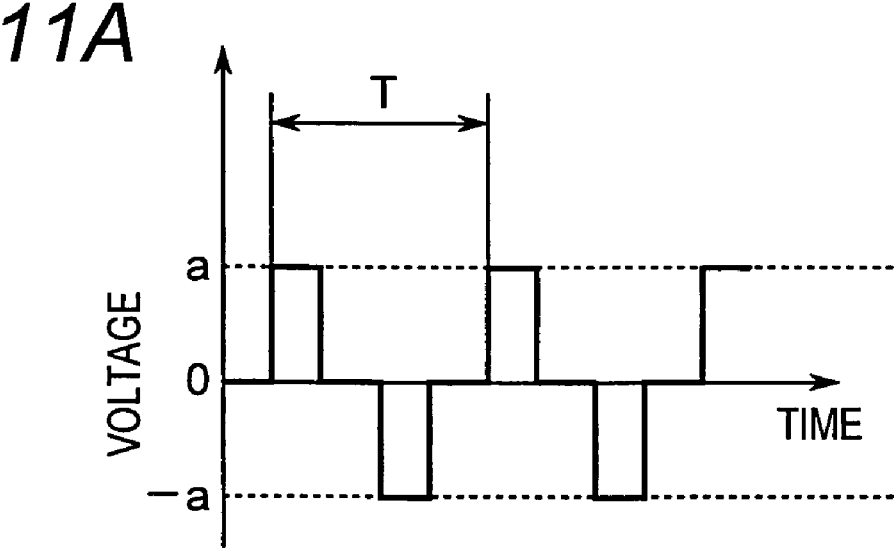
FIG. 11A is a chart showing the waveform of the output voltage when the duty ratio of the pulse is varied.
Figure 11B:
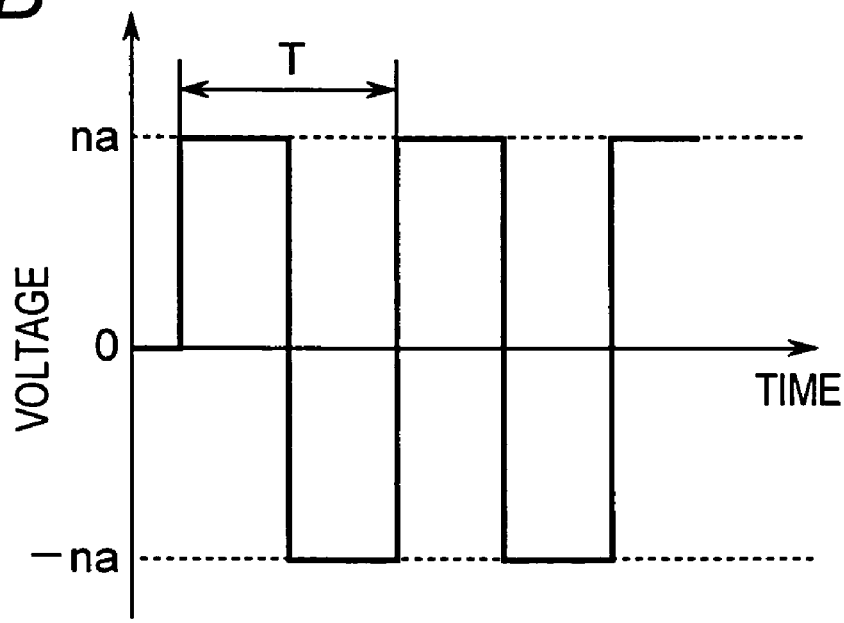
FIG. 11B is a chart showing the waveform of the output voltage when the amplitude of the pulse is varied.
Figure 12A:
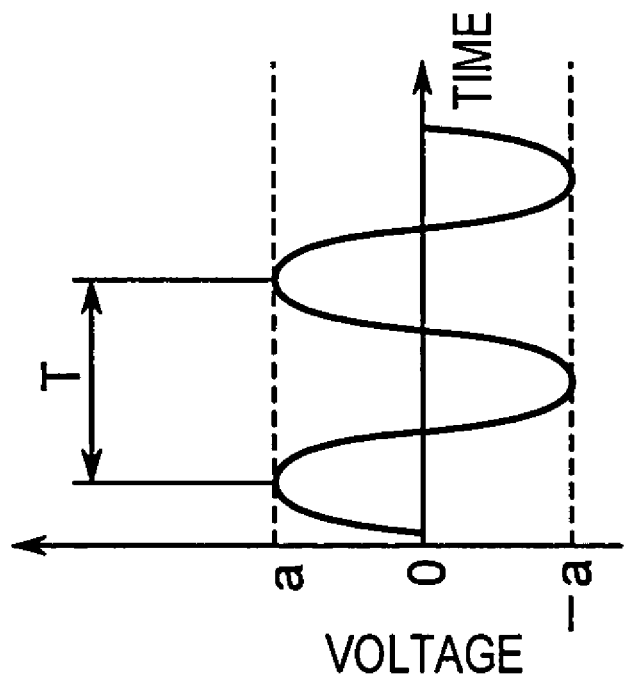
FIG. 12A is a chart showing the waveform of the output voltage when the pulse waveform is changed to a sine waveform.
Figure 12B:
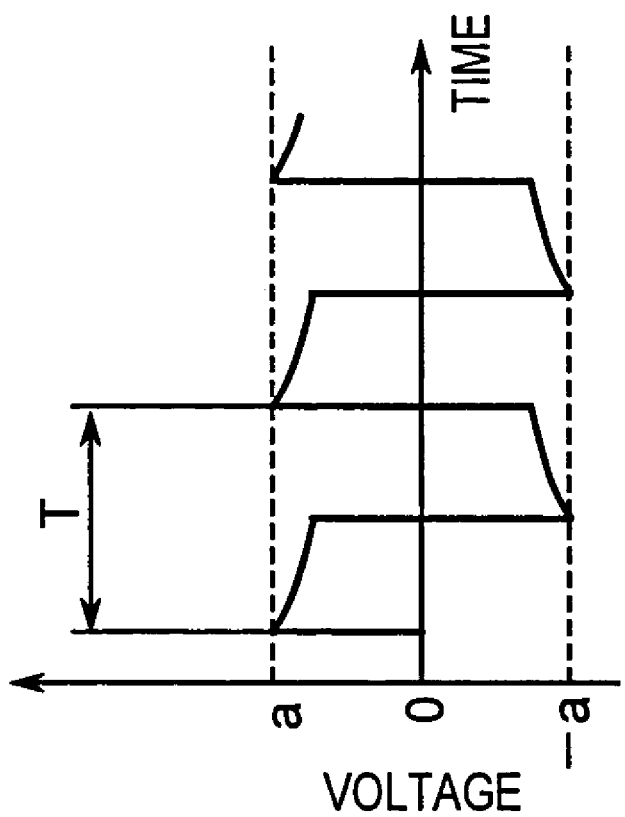
FIG. 12B is a chart showing the output voltage when the pulse waveform is changed to a serrated waveform.

FIG. 10 shows a shape of a pulse waveform of the voltage supplied from the power supply block B1 to the waveform generating circuit block B2. Let it be assumed that the power supply block B1 outputs a pulse of a voltage ranging from +a volt to −a volt at a cycle of T as illustrated therein, to the electric drive energy control circuit of the waveform generating circuit block B2. When the electric drive energy control circuit receives such a voltage pulse, the electric drive energy control circuit modifies, for example, the duty ratio, the amplitude or the kind of the pulse voltage, to thereby provide an output voltage. FIG. 11A shows the waveform of the output voltage where the duty ratio of the pulse voltage is modified. FIG. 11B shows the waveform of the output voltage where the amplitude of the pulse voltage is modified. The term "na" illustrated in the drawing represents n times of the input amplitude a. FIG. 12A shows the waveform of the output voltage where the waveform of the pulse voltage is modified to a sine waveform. FIG. 12B shows the waveform of the output voltage where the waveform of the pulse voltage is modified to a serrated waveform. The electric drive energy control circuit can generate an output voltage by combining the above described pulse waveform treatments in any suitable manner. The electric drive energy control circuit of the waveform generating circuit block B2 can regulates the output voltage in this manner to vary the electric quantity and, accordingly, the amount of displacement of the brush head 17 (illustrated in FIG. 8) that is driven in dependence on the electric energy can be controlled as desired. Accordingly, it is possible to adjust the amount of displacement of the brush head 17 (illustrated in FIG. 8) to suit to the user's liking.

Figure 13:
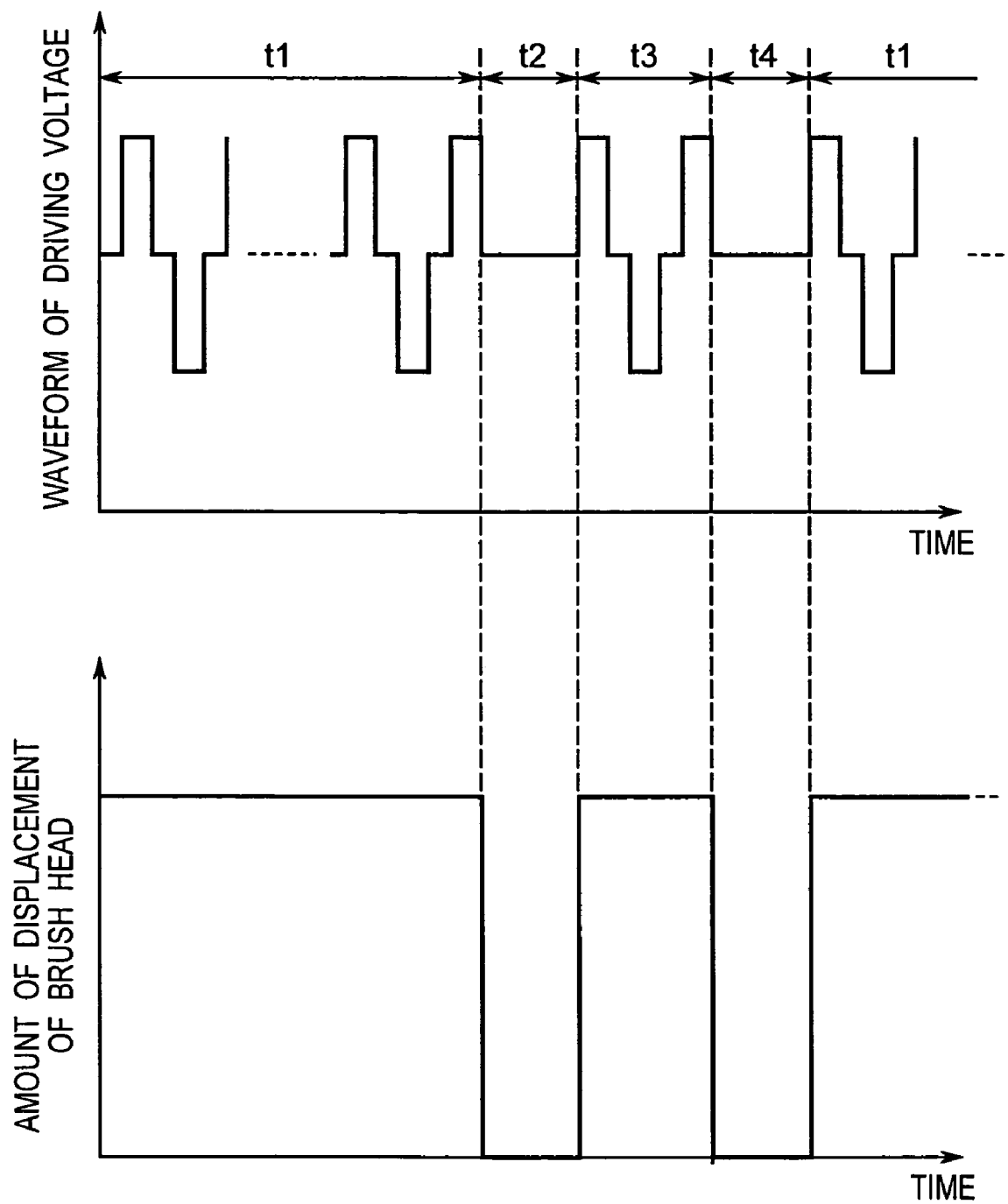
FIG. 13 is a chart showing the waveform of a driving voltage controlled in dependence on the length of time elapsed.

The electric drive energy control circuit of the waveform generating circuit block B2 can still regulates the electric energy in dependence on the length of time. FIG. 13 shows the waveform of a driving voltage that is regulated in dependence on the length of time. When the electric toothbrush 108 (illustrated in FIG. 8) operates the brush head 17 for a predetermined period t1 (for example, 120 seconds), its operation is turned off for the subsequent period t2 (for example, 0.3 seconds). Thereafter, for the third period t3 (for example, 0.3 seconds), its operation is turned on; for the fourth period t4 (for example, 0.3 seconds), its operation is turned off; and, thereafter, its operation is turned on again for the fifth period t1. With the driving voltage regulated in this manner, it is possible to notify the user about the elapse of the predetermined period t1. Accordingly, the user can perceive the length of time passed during the teeth brushing, thereby preventing user's teeth from being brushed scantly or too much.

Figure 14:
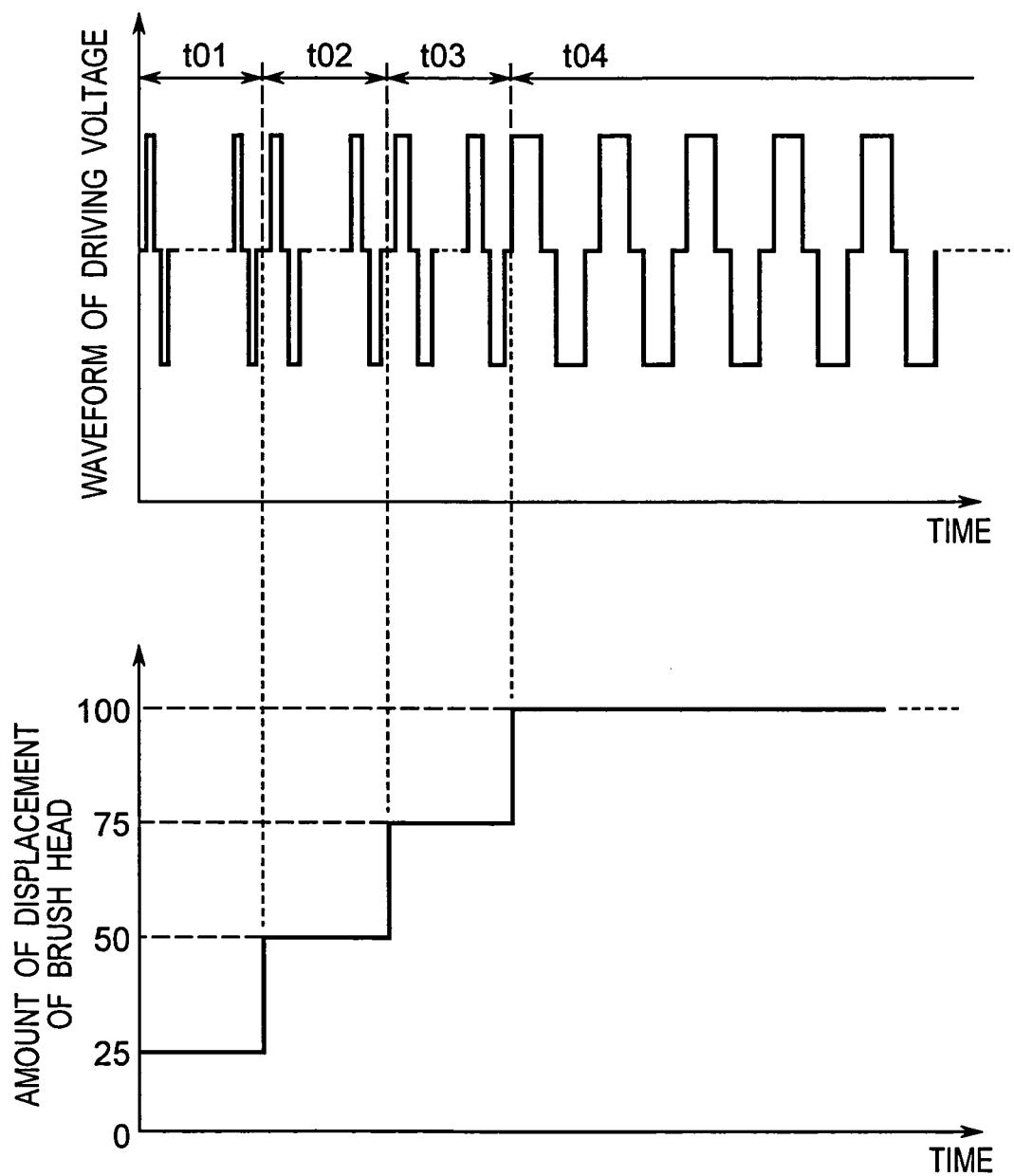
FIG. 14 is a chart showing the relationship between the amount of a gradually increasing displacement of a brush head and the corresponding waveform of the driving voltage.

In addition, the electric drive energy may be regulated in such a way as to gradually increase the amount of displacement of the brush head 17 after the switch 14 (illustrated in FIG. 8) has been manipulated to turn the electric power source on. FIG. 14 shows the relationship between the amount of displacement, which increases gradually, of the brush head 17 and the corresponding driving voltage. It is to be understood that the amount of displacement of the brush head (i.e. its stroke) varies in dependence on the pulse width of the driving voltage. It is to be noted that the pulse width means the period during which the pulse is rising or the period during which the pulse is falling. Since the driving voltage is regulated in this manner, it is possible to diminish the risk of scattering of a tooth powder and water applied to the brush head 17 before the brush 17 is brought in the user's mouth after the power source have been turned on with the tooth powder and water applied on the brush head 17 (illustrated in FIG. 8). The respective symbols t01, t02 and t03 illustrated in the accompanying drawing are preferably approximately 0.6 seconds, but they are not limited to such value.

The invention claimed is:

1. A linear oscillator for reciprocating a shaft in an axial direction of the shaft, comprising:
   a case;
   a plunger disposed in the case so as to be movable together with the shaft in the axial direction of the shaft;
   an elastic member acting in the axial direction of the shaft for applying a resilient force to the plunger;
   an electromagnetic driving unit operable to reciprocate the plunger in the axial direction of the shaft at a resonant frequency when an alternating current is applied thereto;
   the elastic member comprising a coil spring having first and second opposite ends, the first end being fixed with the case and the second end being fixed with the plunger to impart rotation to the shaft about the axis of the shaft within a predetermined angular range concurrently with an axial expansion or contraction of the coil spring caused by the reciprocation of the plunger.

2. The linear oscillator according to claim 1, wherein the electromagnetic driving unit comprises:
   a magnet acting in the axial direction of the shaft for applying a magnetic force to the plunger;
   a coil for varying a magnetic flux density of the magnet in dependence on an electric current flowing therethrough; and
   a control circuit for supplying the alternating current at the resonant frequency to vary a balance between the resilient force of the elastic member and the magnetic force of the magnet, thereby reciprocating the plunger in the axial direction of the shaft.

3. The linear oscillator according to claim 2, wherein the control circuit is operable to regulate a pulse width of an electric power pulse, required to obtain the alternating current, to vary a stroke of reciprocating motion of the plunger in the axial direction of the shaft.

4. The linear oscillator according to claim 3, wherein the control circuit is operable to vary a timing, at which an electric power pulse required to obtain the alternating current is generated, in dependence on a time elapsed from a start of the reciprocating motion of the plunger.

5. The linear oscillator according to claim 3, wherein the control circuit is operable to gradually increase a pulse width of an electric power pulse, required to obtain the alternating current, in dependence on a time elapsed from a start of the reciprocating motion of the plunger, thereby increasing a stroke of the reciprocating motion of the plunger in the axial direction of the shaft.

6. The linear oscillator according to claim 2, wherein the control circuit is operable to vary a timing, at which an electric power pulse required to obtain the alternating current is generated, in dependence on a time elapsed from a start of the reciprocating motion of the plunger.

7. The linear oscillator according to claim 2, wherein the control circuit is operable to gradually increase a pulse width of an electric power pulse, required to obtain the alternating current, in dependence on a time elapsed from a start of the reciprocating motion of the plunger, thereby increasing a stroke of the reciprocating motion of the plunger in the axial direction of the shaft.

8. The linear oscillator according to claim 1, wherein the predetermined angular range is less than about 10 degrees.

9. An electric toothbrush having a linear oscillator for reciprocating a shaft in an axial direction of the shaft and a brush head attached to the shaft for use in brushing teeth, the linear oscillator comprising:
   a case;
   a plunger disposed in the case so as to be movable together with the shaft in the axial direction of the shaft;
   an elastic member acting in the axial direction of the shaft for applying a resilient force to the plunger;
   an electromagnetic driving unit configured for reciprocating the plunger in the axial direction of the shaft at a resonant frequency when an alternating current is applied thereto;
   the elastic member comprising a coil spring having first and second opposite ends, the first end being fixed with the case and the second end being fixed with the plunger to impart rotation to the shaft about the axis of the shaft within a predetermined angular range concurrently with an axial expansion or contraction of the coil spring caused by the reciprocation of the plunger.

10. The linear oscillator according to claim 9, wherein the electromagnetic driving unit comprises:
    a magnet acting in the axial direction of the shaft for applying a magnetic force to the plunger;
    a coil for varying a magnetic flux density of the magnet in dependence on an electric current flowing therethrough; and
    a control circuit for supplying the alternating current at the resonant frequency to vary a balance between the resilient force of the elastic member and the magnetic force of the magnet, thereby reciprocating the plunger in the axial direction of the shaft.

11. The electric toothbrush according to claim 10, wherein the control circuit is operable to regulate a pulse width of an electric power pulse, required to obtain the alternating current, to vary a stroke of reciprocating motion of the plunger in the axial direction of the shaft.

12. The electric toothbrush according to claim 11, wherein the control circuit is operable to vary a timing, at which an electric power pulse required to obtain the alternating current is generated, in dependence on a time elapsed from a start of the reciprocating motion of the plunger.

13. The electric toothbrush according to claim 11, wherein the control circuit is operable to gradually increase a pulse width of an electric power pulse, required to obtain the alternating current, in dependence on a time elapsed from a start of the reciprocating motion of the plunger, thereby increasing a stroke of the reciprocating motion of the plunger in the axial direction of the shaft.

14. The electric toothbrush according to claim 10, wherein the control circuit is operable to vary a timing, at which an electric power pulse required to obtain the alternating current is generated, in dependence on a time elapsed from a start of the reciprocating motion of the plunger.

15. The electric toothbrush according to claim 14, wherein the control circuit is operable to gradually increase a pulse width of an electric power pulse, required to obtain the alternating current, in dependence on a time elapsed from a start of the reciprocating motion of the plunger, thereby increasing a stroke of the reciprocating motion of the plunger in the axial direction of the shaft.

16. The electric toothbrush according to claim 10, wherein the control circuit is operable to gradually increase a pulse width of an electric power pulse, required to obtain the alternating current, in dependence on a time elapsed from a start of the reciprocating motion of the plunger, thereby increasing a stroke of the reciprocating motion of the plunger in the axial direction of the shaft.

17. The electric toothbrush according to claim 9, wherein the predetermined angular range is less than about 10 degrees.

* * * * *

UNITED STATES PATENT AND TRADEMARK OFFICE
CERTIFICATE OF CORRECTION

| | | |
|---|---|---|
| PATENT NO. | : 7,315,098 B2 | Page 1 of 1 |
| APPLICATION NO. | : 10/472188 | |
| DATED | : January 1, 2008 | |
| INVENTOR(S) | : Kunita et al. | |

It is certified that error appears in the above-identified patent and that said Letters Patent is hereby corrected as shown below:

At column 10, line 26 of the printed patent, "The linear oscillator" should be --The electric toothbrush--.

Signed and Sealed this

Twenty-seventh Day of October, 2009

David J. Kappos
*Director of the United States Patent and Trademark Office*